(12) United States Patent
Woelders

(10) Patent No.: US 6,303,285 B1
(45) Date of Patent: Oct. 16, 2001

(54) APPARATUS AND METHOD FOR FREEZING LIVE CELLS

(75) Inventor: Henri Woelders, Bunnik (NL)

(73) Assignee: Stichting Dienst Landbouwkundig Onderzoek (NL)

( * ) Notice: Subject to any disclaimer, the term of this patent is extended or adjusted under 35 U.S.C. 154(b) by 0 days.

(21) Appl. No.: 09/308,916

(22) PCT Filed: Nov. 26, 1997

(86) PCT No.: PCT/NL97/00648

§ 371 Date: Oct. 6, 1999

§ 102(e) Date: Oct. 6, 1999

(87) PCT Pub. No.: WO98/23907

PCT Pub. Date: Jun. 4, 1998

(30) Foreign Application Priority Data

Nov. 26, 1996 (NL) .................................................. 1004619

(51) Int. Cl.⁷ ................................. A01N 1/00; C12M 1/00
(52) U.S. Cl. ............................ 435/1.3; 435/2; 435/283.1
(58) Field of Search ................................. 435/1.3, 283.1, 435/2

(56) References Cited

U.S. PATENT DOCUMENTS

| | | | |
|---|---|---|---|
| 3,753,357 | * | 8/1973 | Schwartz . |
| 4,480,682 | * | 11/1984 | Kaneta et al. . |
| 4,712,607 | * | 12/1987 | Lindemans et al. . |
| 4,799,358 | * | 1/1989 | Knopf et al. . |
| 5,814,078 | * | 9/1998 | Zhou et al. . |

FOREIGN PATENT DOCUMENTS

| | | |
|---|---|---|
| 0 117 037 A | 8/1984 | (EP) . |
| 0 150 146 A | 7/1985 | (EP) . |
| 0 181 235 A | 5/1986 | (EP) . |
| 0 275 829 A | 7/1988 | (EP) . |
| 7 215 535 A | 5/1973 | (NL) . |

* cited by examiner

Primary Examiner—Leon B. Lankford, Jr.
(74) Attorney, Agent, or Firm—TraskBritt

(57) ABSTRACT

An apparatus for freezing live cells, in particular sperm, which cells are included in at least one sample in at least one container, wherein means are provided for cooling the or each container, wherein the cooling means (5, 6, 7; 105, 106, 107) comprise at least one contact face (3, 103), capable of being cooled, for cooling, during use, the or each container (16, 116) and the or each sample included therein through abutting contact, wherein control means (10, 110) are provided for controlling, during cooling, the cooling rate (TG) and the ambient temperature of the or each container (16, 116).

20 Claims, 4 Drawing Sheets

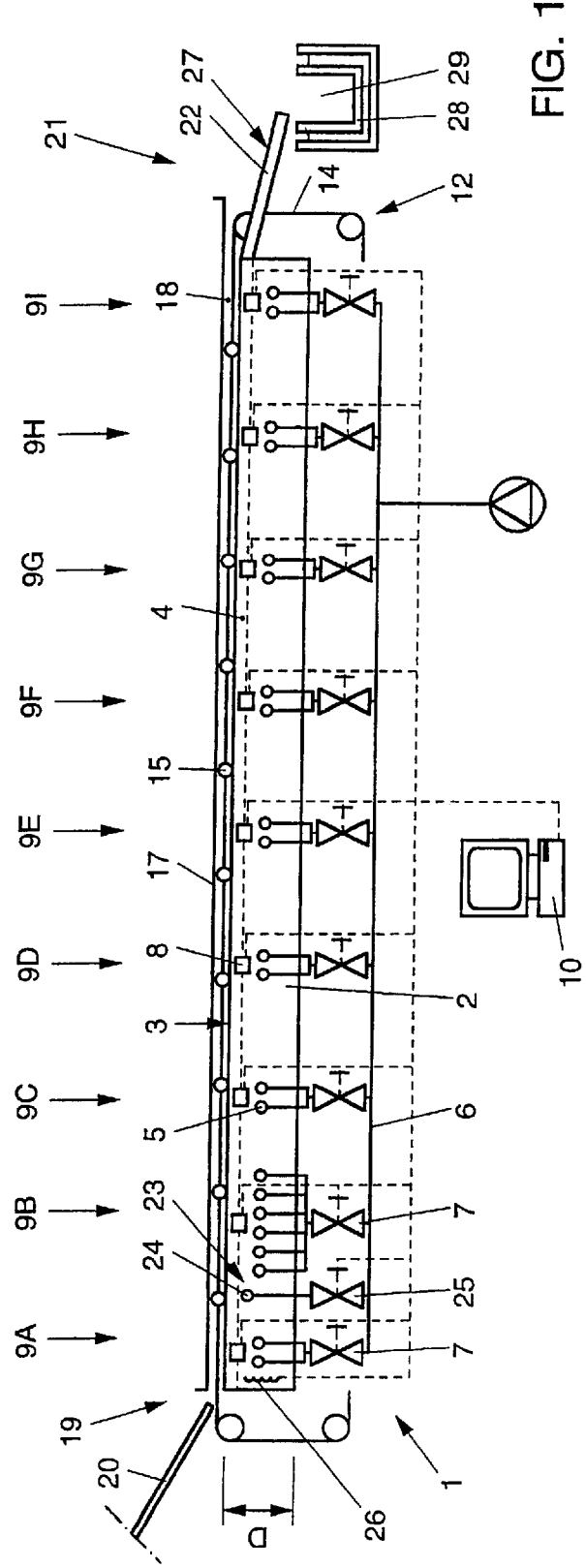
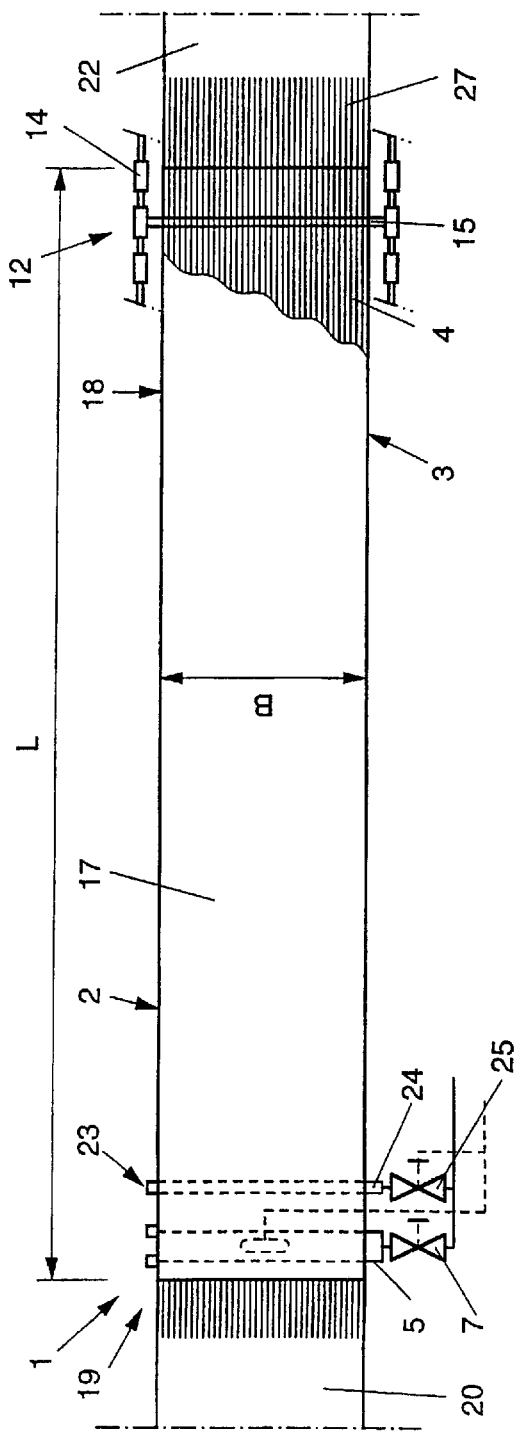
FIG. 1
FIG. 2

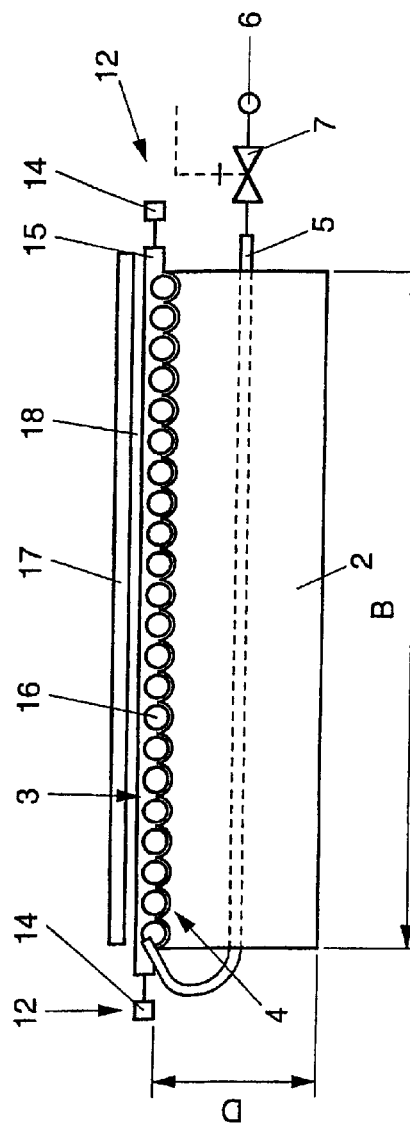
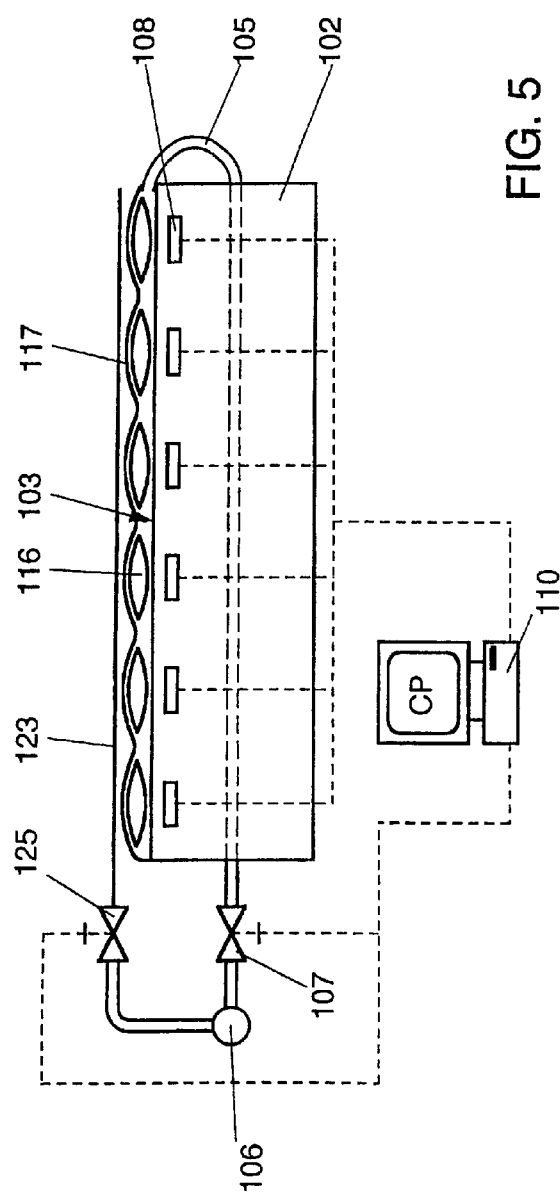

APPARATUS AND METHOD FOR FREEZING LIVE CELLS

The invention relates to an apparatus and method for freezing live cells, in particular sperm, according to the preamble of claim 1. Such known apparatus is known from EP 0 117 037.

Apparatus for freezing live cells, in particular for freezing sperm, are used for storing cells in living condition for later use. To that end, a sample comprising for instance a number of sperm cells in a liquid solution is introduced into a container and cooled so that freezing occurs. In this specification, the apparatus and method will be described on the basis of sperm samples, yet the invention should not be construed as being limited thereto. Many other live cells can be treated in a like manner or with like means, with like advantages.

A known apparatus comprises a vessel into which liquid nitrogen can be introduced, for cooling the contents of the vessel. In samples of a slight volume, the sperm is introduced into a straw or a like relatively thin, tubular container, after which a large number of filled containers are simultaneously introduced into the vessel and cooled. When complete freezing of the contents has taken place, the containers are removed from the vessel and stored at a storing temperature, suitable for later use for, for instance, artificial insemination.

The temperature change occurring in the vessel and in the containers is substantially determined by the type and temperature of the containers when being introduced into the vessel, the number of containers and the temperature in the vessel when the containers are being introduced therein. Moreover, research by applicant has shown that the heat development in the containers resulting from the crystallization occurring therein contributes significantly to the change of the temperature in the containers. This change proves to be of particular importance for the result of the freezing of the sample, in particular for the chances of survival and the vitality of the cells after passing through the method and a subsequent thawing. The above research has demonstrated that in this respect, in particular the temperature change in the sample during the occurrence of crystallization is of great importance.

In the known apparatus, it is not possible to accurately control the change of the temperature in the separate containers. During the use of such apparatus, relatively great differences will occur in the change of temperature in the different containers, for instance due to the position of the containers relative to each other and to the vessel and due to differences in the presence of crystallization nuclei in the sample and, accordingly, differences in the phase in which crystallization occurs. Due to the fact that when a known apparatus is employed for freezing for instance one ejaculate, from which a very large number of containers can be filled, these influences cannot be removed or controlled, such apparatus is economically not very advantageous and the usability of each sample is adversely affected.

EP 0 117 037 discloses an apparatus for freezing live cells, such as fertilized ova, spermatozoa and the like, comprising a cylindrical outer wall connected to a disk shaped bottom plate through which cooling channels extend. Centrally, concentric within said cylindrical outer wall a cylindrical inner wall has been provided which is thermically isolated from said bottom plate by an insulating ring. The lower part of the inner cylinder is made of copper and comprises a second cooling channel, spiralling around a heating element. Between said cylindrical inner wall and said cylindrical outer wall a ring shaped space extends into which straw like tubes, containing the live cells to be frozen, can be positioned. Within the upper part of the inner cylindrical wall an open container has been provided containing liquid nitrogen for containing the holders with frozen samples. Control means have been provided for supplying and discharging a cooling liquid such as nitrogen to the specific cooling channels and for controlling said heating element. Temperature sensors have been provided in the bottom plate and the ring shaped holding space. The object of this known apparatus is to execute a method according to Japanese patent application No. 124996/1981 of the same applicant, in which method crystallization nuclei has to be achieved within a buffer solution, distanced from the living cells therein, such as to prevent thermical shock to said living cells.

This known apparatus can only contain a limited number of containers, which containers have to be prepared such that a space containing only buffer solution, no live cells, is provided near the lower end, for initiating freezing. With such known apparatus freezing of live cells will therefore be time consuming and costly.

The object of the invention is to provide an apparatus for freezing live cells, in particular sperm, in which the above drawbacks of the known apparatus are avoided, while the advantages thereof are maintained. To that end, an apparatus according to the invention is characterized by the features of claim 1.

In this specification, temperature gradient should be interpreted as a spatial change of the temperature (°C./cm). Where a temperature change in time is meant, this change will be referred to as temporal gradient, cooling rate, variation in temperature or a like, time-related term (°C./min).

Because of the or each contact face to be cooled, by means of which the or each container, by resting thereon, can be cooled, the advantage is achieved that a proper control of the temperature of the or each container, and accordingly of the or each sample, can be realized regardless of the number of containers to be cooled. The control means provide the possibility of accurately controlling the temperature and the change thereof during the entire cooling or freezing path over which the containers are moved for providing for the desired temporal gradient within the containers. As a result of the accurate control of the temperature, in particular the change thereof during the freezing path, more cells survive freezing and the subsequent thawing, while, moreover, the surviving cells have a better vitality. An important additional advantage is that due to the greater percentage of surviving, more vital cells, fewer sperm cells have to be included into a sample, while the same sample quality is maintained for use in artificial insemination. This means that a greater dilution of an ejaculate can be carried out, as a result of which more containers can be filled per ejaculate. This means that a better economical efficiency is obtained and that, moreover, at least as far as sperm is concerned, more female animals can be fertilized from one ejaculate, which has for instance operational advantages to the owner or at least the holder of both the male and the female animal.

Moreover, the chance of a successful insemination with a sample from an ejaculate which in the starting situation has very few vital cells is greater, which is of substantial importance in particular with respect to, for instance, humans, particular species of animals, and the like.

During cooling, ice formation within the cells (intracellular ice formation) should be prevented in particular near the freezing point or path of the solution, because this is fatal to the cells in question. The cause of the prevention thereof is an efflux of water from the cell, i.e. water flowing away through the cell membrane to the environment. As a consequence, the water concentration in the cell decreases, i.e. the proportion of water in the cell volume becomes less, so that the freezing point falls.

In the case of unduly high cooling rates, the efflux of water will take place very rapidly, which in itself already seems unfavorable for the cells. Moreover, there is a substantial chance that the water efflux, relative to the cooling rate, does not take place rapidly enough, i.e. the freezing point falls less quickly than the temperature. As a consequence, the temperature falls far below the freezing point, so that intracellular ice is formed all the same.

Conversely, in the case of unduly low cooling rates, the reverse effect occurs. The ice crystallization outside the cells (intercellular) and the efflux of water from the cells can proceed calmly, so that these processes will near the thermodynamic equilibrium. This equilibrium is at a very low water concentration in the cells. Hence, dehydration will occur very rapidly, intercellularly as well as intracellularly. Dehydration and concentrations of salt and metabolite in the cells become so high that the cells are damaged thereby. Moreover, the cells become deformed through decrease of the volume, and damaged by the rapidly growing intercellular ice crystals. Further, in the case of an unduly low freezing rate, the cells remain too long in the unstable condition. Only at very low temperatures, for instance below −80° C., will no (bio)chemical reactions or physical transitions take place anymore.

Through a suitable selection of the temperature profile during the cooling path, a momentary cooling rate can in each case be realized such that the above drawbacks are avoided. Such control of the temperature change is readily enabled by the use of an apparatus according to the invention.

In an advantageous embodiment, an apparatus according to the invention is characterized by the features of claim 2.

The means for moving the containers relative to the or each contact surface offer the advantage that (semi) continuous cooling of the containers and the samples included therein can thereby be obtained, while the cooling period is for instance determined by the period of movement of the containers along the or each contact face. Moreover, this prevents in a simple and suitable manner the containers from getting stuck in the apparatus, for instance in that the containers freeze fast thereto.

In an advantageous further elaboration, an apparatus according to the invention is further characterized by the features of claim 3.

The temperature difference between the beginning and the end of the path of movement, with the or each container, during use, being moved in the direction of the coldest end, offers the advantage that a gradual cooling of the containers can thereby be obtained. Moreover, the control means offer the possibility, through the control of the temperature gradient over the or each contact face, of providing a temperature profile over the path of movement of the or each container. Together with the control of the rate of the or each container relative to the apparatus, in particular relative to the or each contact face, an optimal freezing profile for the relevant live cells can thus be set for each container and, accordingly, for each sample. It will be understood that in this regard, it is preferred that at the coldest end of the apparatus, each sample has been frozen to a sufficient extent.

During the freezing of live cells, applicant's research demonstrated that the occurrence of crystallization in a sample is of great influence on the result of the freezing method, in particular on the chances of survival and the vitality of sperm cells. In this connection, it is in particular of importance that the moment when the crystallization starts and the change of the temperature are properly controlled.

It has been found that the moment of occurrence of the crystallization is of utmost importance. If the crystallization is started too late, the cells, at least a portion thereof, are delayed too long in an unfavorable, unstable situation, between 0° C. and −5° C.

In order to avoid these drawbacks, an apparatus according to the invention is characterized by the features of claim 4.

During use, the movement of each container is controlled by means of the control means in such a manner that the occurrence of crystallization in a sample, in a so-called crystallization phase, at least substantially takes place in that portion of the apparatus where a relatively slight temperature difference prevails between the beginning and the end of the portion in question, a crystallization sector. The heat emitted by the or each sample during the crystallization phase provides a slight rise of temperature in the container in question, the crystallization occurs relatively slowly, with crystals being formed in an advantageous manner, and any exchange of, for instance, ions and water between the cells and the environment takes place relatively gradually, as a result of which no shock effects occur. Partly because of this, a better result is obtained with an apparatus according to the invention than when the known apparatus is used. If crystallization is not initiated, the entire sample should be highly supercooled. When the crystallization occurs, a very strong rise of temperature will then occur, resulting in a temperature shock, while sudden crystallization will occur. This causes, inter alia, mechanical shocks, which may damage the cells. There will further occur a sudden change in the osmotic pressure and the ion strength, and an unduly fast water transport through cell membranes.

Important advantages of initiating the crystallization can be understood as follows.

As soon as crystallization starts, the temperature in the relevant cells or parts of the sample will shift to the freezing point applying to the relevant solution. As long as the crystallization is not at least largely complete, the temperature in the container can hardly, if at all, be influenced from outside, other than by keeping the crystallization going. In the known methods and apparatuses, the ambient temperature is further reduced each time also during the occurrence of the crystallization, cooling is continued. Surprisingly, it has been found that this ambient temperature should in fact fall only minimally, if at all, during the crystallization, to prevent undue temperature differences between the contents of the container and the environment. If this difference becomes too great, substantial spatial differences may occur in the progress of the crystallization, for instance between a zone adjacent the outer wall of the container and a zone in the heart of the container. Such undesired differences will also cause undesired differences in cooling rate. Moreover, a cooling of the environment which is continued during the crystallization has as a consequence that when the crystallization is complete, the temperature difference between the container and the environment is unacceptably great, causing the subsequent cooling to proceed too fast.

When an apparatus according to the invention is used, a crystallization phase further offers the advantage that, if so desired, the cooling path preceding the crystallization phase and in particular the following cooling path to a storing temperature can proceed relatively rapidly, so that with an apparatus according to the invention, a large number of samples can be frozen quickly.

In a further advantageous embodiment, an apparatus according to the invention is characterized by the features of claim 7.

The modules may all be substantially identical, allowing them to be manufactured at relatively low costs. Thus, a large number of modules can be employed at relatively slight costs. This offers the advantage that during use, the temperature differences between the modules can be slight, while the modules need have relatively little mass and can yet discharge sufficient heat. For instance, the modules may be built up from blocks comprising cooling means and made from substantially solid aluminum or a like material. In this respect, it is preferred that for each module there are provided separate control means for controlling at least the temperature thereof. Thermal coupling of the modules provides a gradual change of the temperature along the surface which is formed from the joint contact surfaces and along which the containers are moved.

As a matter of fact, a contact surface of an apparatus according to the invention may also substantially be of a one-piece construction, for instance as a side of a relatively thick, solid block of aluminum or the like having cooling means, while a number of cooling stations are provided, spaced apart a relatively large distance. The temperature difference between successive cooling stations may be relatively great, while, moreover, fewer cooling stations are required than in the case of a modular and/or relatively thin embodiment, which may offer economical advantages.

In further elaboration, an apparatus according to the invention is further characterized by the features of claims 10 and 11.

The cooling channels according to the invention enable a particularly simple and economically advantageous cooling of the or each contact surface, while a precise positioning and dimensioning of the cooling channels may moreover bring about a very good distribution of the temperature and a good temperature gradient over the relevant contact face. The use of a cooling medium which evaporates when leaving the cooling channels, and the discharge of the produced vapor through the substantially closed housing along the containers, prevent the flow of air into the housing and the precipitation of at least moisture therefrom on the containers and/or the contact surface. Such condensation and the subsequent freezing of air, at least moisture, will impede a proper feed-through of the containers and, moreover, this is disadvantageous from an energetic point of view. In addition, this may cause contamination of the or each contact surface.

In a preferred embodiment, an apparatus according to the invention is further characterized by the features of claim 15.

As described hereinabove, it is of great importance that the crystallization takes place substantially during the crystallization phase, preferably under strictly controlled conditions. The start of the crystallization is in many cases a chance process, depending on, inter alia, the presence of nucleation centers. The crystallization-initiation means according to the invention have the advantage that the crystallization is started, controlled thereby, at that moment in the freezing process which is the most suitable for the relevant cells. The crystallization-initiation means are preferably designed as means for temporarily and locally supercooling a container at the beginning of the crystallization phase.

The invention further relates to a method for freezing live cells, characterized by the features of claim 16.

Further advantageous embodiments of an apparatus and method according to the invention are represented in the subclaims and the specification.

To clarify the invention, exemplary embodiments of an apparatus according to the invention and a method will hereinafter be described, with reference to the accompanying drawings. In these drawings:

FIG. 1 is a side elevational view of an apparatus according to the invention;

FIG. 2 is a top plan view of an apparatus according to FIG. 1, with top cover partially removed;

FIG. 3 is a front view of an apparatus according to FIG. 1;

FIG. 5 is a side elevational view of an alternative, stationary embodiment of an apparatus according to the invention.

Figure 4:
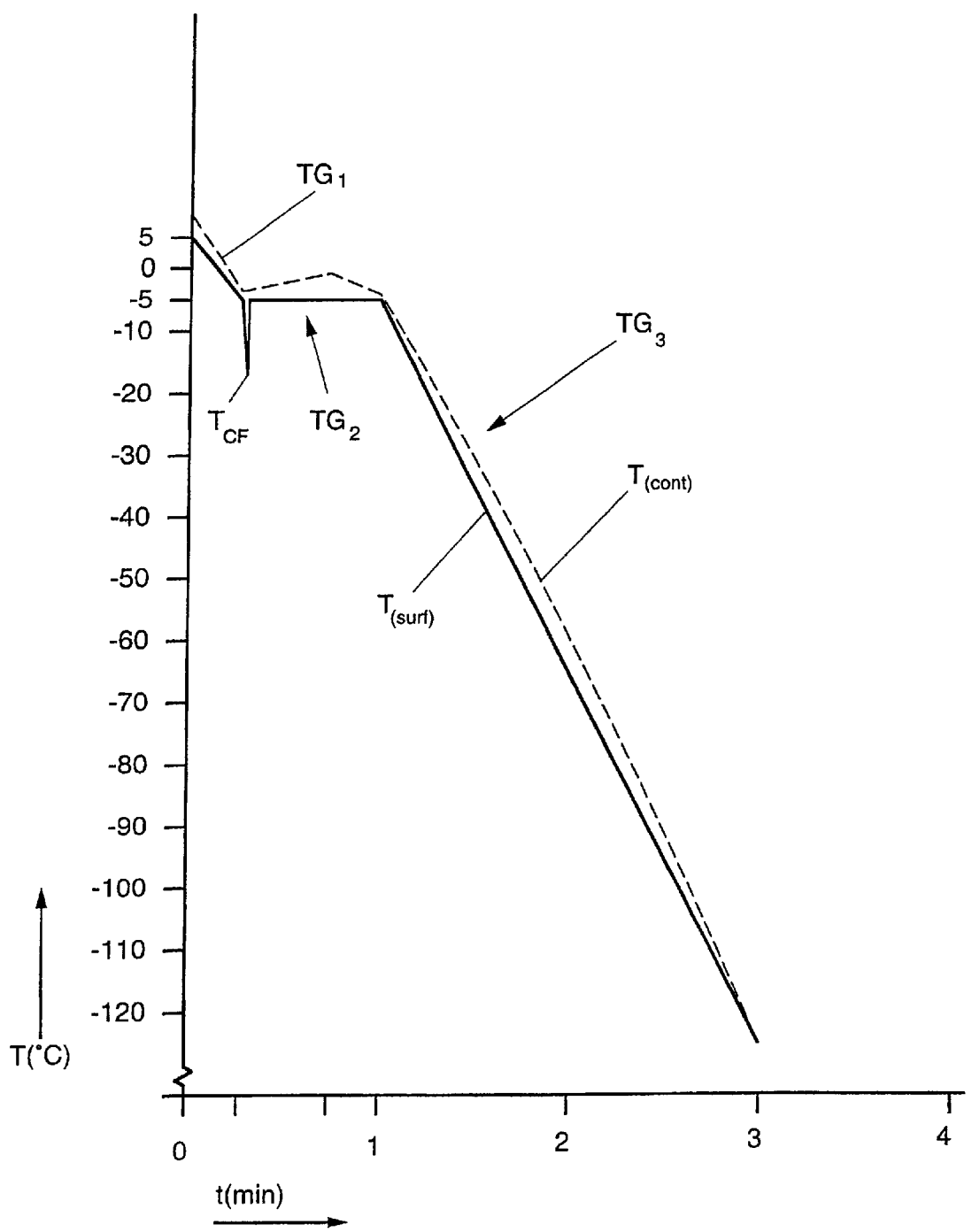
FIG. 4 is a schematic representation of a time-temperature protocol for an apparatus according to FIGS. 1–3.

An apparatus 1 according to FIGS. 1–3 comprises a block 2 manufactured from heat-conducting material, for instance aluminum or an aluminum alloy. The block 2 has a great length L relative to its width B, while the thickness D is relatively small. The top side 3 of the block 2 is provided with a series of parallel, longitudinally extending grooves 4 whose purpose and embodiment will be explained in more detail hereinbelow.

Extending through the block 2, below the top face 3, are a number of cooling pipes 5, substantially transverse to the longitudinal direction of the block 2 and throughout the width B thereof. A number of juxtaposed cooling pipes 5 are in each case jointly connected to a feed pipe 6 for a cooling medium, for instance liquid nitrogen. Included in each feed pipe is a control valve 7 for dosing the amount of cooling medium that is passed through the relevant cooling pipes 5. The control valve 7 is controlled by a thermostat or other types of temperature-measuring means 8 provided in the surface 3 at the location of the relevant cooling pipes 5. The cooling pipes 5 that are jointly fed by one feed pipe 6 and one control valve together form one cooling station 9, in which the temperature is controlled on the basis of signals from the associated temperature-measuring means 8. In the embodiment shown, nine of such cooling stations 9A–9I are provided one behind the other, viewed in the longitudinal direction of the block 2.

The temperature-measuring means 8 are jointly settable by means of a central control unit 10, by means of which the desired temperature can be set in each cooling station 9, in such a manner that a desired temperature profile over the block 2 can be obtained. This desired temperature profile will be explained in more detail hereinbelow.

The apparatus comprises a drive device 12, comprising a chain or belt 14 having push rods 15 which extend over the top face 3 of the block 2, over the grooves 4.

During use, a number of containers 16 lie in the grooves 4 in such a manner that the containers 16 have a part of their outer surfaces resting against the inner surface of the grooves 4, as is clearly demonstrated in FIG. 3. In the exemplary embodiment shown, the containers 16 are formed by thin-walled straws in which a sample is included. Each sample comprises a number of live cells to be frozen, in particular sperm, in a quantity of dissolving liquid. The straws are juxtaposed in longitudinal direction, with a push rod 15 in each case abutting against the end of the containers 16 trailing in direction of movement. Hence, during the drive of the drive device 12, the containers are moved in the longitudinal direction through the grooves 4 between the two ends of the block 2, while making close contact with the surface 3 of the block 2, in particular the insides of the grooves 4.

Provided over the top face 3 of the block 2 is a thin, flexible and thermally insulating film 17, for instance HDPE- or PTFE-film. This film 17 insulates the containers 16 from the environment and together with the block 2 forms a closed housing 18. At for instance the side remote from the feed pipe 6 or through small passages to the grooves 4, the cooling channels 5 open below the film 17, within this housing 18. Upon leaving the cooling pipes 5, the liquid nitrogen evaporates and displaces all air from the housing 18 or at least between the film 17 and the surface 3 of the block 2. This prevents the occurrence of condensation within the housing 18, which condensation could have as a consequence that the containers 16 cannot be pressed through the grooves 4 in a regular manner, if at all. Moreover, condensation is thermally unfavorable. In this regard, it is preferred that the evaporating medium flows in the direction of the feed-in end 19, i.e. the warmest end of the apparatus, so that the containers are not warmed up again thereby unintentionally. Moreover, any air within the apparatus will tend to flow along in the direction of movement of the containers 16. For that reason, it is advantageous to cause the nitrogen to flow substantially in opposite direction for displacing that air. However, by causing a relatively small portion of the nitrogen to move along with the containers 16, the air adjacent the cold end of the apparatus is expelled as well.

In the second cooling station 9B, a so-called cooling finger 23 is provided as crystallization-initiation means. In the embodiment shown, this cooling finger 23 comprises a tubular part 24 connected to the cooling medium feed pipe 6. The tubular part 24 lies in the surface 3 of the block 2 in such a manner that the containers 16 come into contact therewith when passing it. By means of a control valve 25, liquid nitrogen can be driven through the tubular part 24, whereby the cooling finger 23 can be made cold suddenly and briefly, i.e. colder than the surface 3 around the finger 23 in the relevant cooling station 9B. The purpose hereof will be explained in more detail hereinbelow.

At the feed end 19 of the block 2, i.e. the upstream end in direction of conveyance, there is arranged a feeder 20 which provides a regular distribution of the straws 16 over the surface 3 of the block 2, and which in particular provides the positioning of the straws 16 into the grooves 4. Such feeder 20 can be constructed in many different manners.

At the discharge end 21 of the block 2, a discharge device 22 is connected, which provides the sorting and storage of the straws with samples frozen therein. Such discharge device 22, too, can be constructed in many different manners.

An apparatus according to FIGS. 1–3 may for instance have the following dimensions, which dimensions should not be construed as being limitative in any way. The block may have a length L of 1600 mm, a width B of 300 mm and a thickness of some tens of millimeters. In the surface 3, there may be provided 100 channel-shaped grooves 4 having a width of 3 mm. During use, for instance 100 straws can be disposed side by side and 11 straws can be disposed behind each other on the surface 3 of the block 2.

FIG. 4 schematically shows a temperature graph for an apparatus according to FIGS. 1–3. A drawn line $T_{(surf)}$ shows the temperature profile obtained during use on the surface 3, a broken line $T_{(cont)}$ shows the temperature profile occurring in a container 16 passed over the surface. The lower horizontal axis shows the corresponding cooling stations 9A–9I. During use, the containers 16 are passed over the surface 3 at a rate of, for instance, 1000 mm/min.

In a first cooling station 9A, a temperature $T_1$ is set which, on average, is about +5° C. For that purpose, a heating spiral 26 is provided in this first cooling station 9A, which heating spiral can be switched on when the thermostat 8 in the relevant cooling station 9A registers a temperature below a minimum limit temperature.

In the second cooling station 9B, a temperature $t_2$ is set which is about −5° C. The second cooling station 9B is located at a distance of about 200 mm from the cooling means of the first cooling station 9A, so that between these two cooling stations 9A and 9B a temperature gradient $TG_1$ of about 50° C./min is obtained. The second cooling station 9B has a length of about 350 mm and a temperature which is approximately equal throughout its length. To that end, in the second cooling station 9B, cooling tubes 5 are arranged below the entire surface 3 at regular, relatively small intermediate distances, as opposed to the other cooling stations 9, where cooling tubes 5 are provided below a portion of the surface 3 only.

As the containers enter the second cooling station 9B, they pass the cooling finger 23. When the trailing end of each relevant container 16 is located approximately above the cooling finger 23, the control valve 25 is briefly opened and the cooling finger 23 is highly supercooled. In FIG. 4, this high supercooling of the surface 3 at the beginning of the second cooling station 9B is represented by a dip $T_{cf}$ in the drawn line $T_{(surf)}$. As a result, crystallization is initiated in the containers 16, at a distance from the centers thereof, after which, while the second cooling station 9B is being moved through, complete crystallization can take place in the containers 16. The substantially constant temperature (the minimum temperature gradient $TG_2$) in the second cooling station 9B provides a crystallization pause. In the second cooling station, due to dissipation of crystallization heat, the temperature in the containers may increase to near 0° C.

During use, the ambient temperature of the containers in the second cooling station 9B is set accurately, depending on the type of cells in question. For instance, when used for freezing bovine sperm, the temperature in the second cooling station 9B is set at about −5° C. and kept constant. However, this temperature may also slightly decrease in the second cooling station 9B, i.e. in the relevant second cooling station 9B a low temperature gradient $TG_2$ can be set.

In the part of the apparatus connecting to the second cooling station 9B, a temperature gradient $TG_3$ is preferably set which is higher than that in the preceding part of the apparatus, for instance a temperature gradient or temperature profile which provides a cooling rate of 100° C./min. To that end, in the subsequent cooling stations 9C–9I, temperatures are successively set of $T_3=-15°$ C., $T_4=-25°$ C., $T_5=-40°$ C., $T_6=-55°$ C., $T_7=-75°$ C., $T_8=-95°$ C., and $T_9=-120°$ C. The distance between each of the successive cooling stations is on average for instance about 150 mm.

The specific heat of the ice formed in the containers 16 is considerably less at lower temperatures. For this reason, the distance between two later cooling stations, viewed in the direction of movement, can be relatively great compared with the distance between two earlier cooling stations 9, while the temperature differences between later cooling stations can moreover be greater. Further, for the live cells, in particular for sperm cells, the temperature gradient TG or at least the actual cooling rate at lower temperatures is less critical for the chances of survival of the cells. The thermal conduction of the block 2 should be chosen so, for instance through the choice of material and dimensions, that the heat flow between the cooling stations 9 is considerably greater than the amount of heat emitted by the containers 16 in the relevant cooling stations 9. As a result, a sufficient linear temperature gradient is obtained in the cooling stations 9A and 9C–9I.

The discharge device 2 comprises for instance a number of chutes 27 connecting to receptacles 29 which are arranged in cooling means 28 and in which containers can be sorted and stored. The sorting of the containers may take place prior to the freezing operation, but may also be carried out in the discharge device 22. This can be performed by hand as well as by mechanical sorting means.

In the apparatus described hereinabove, for instance 700 containers 16 can be fed onto the belt per minute, which means that an ejaculate can be processed entirely in about 3–4 minutes.

Starting from the use of identical material for the block 2, it can be stated that a thicker block 2 can offer the advantage of necessitating fewer cooling stations, which may be spaced apart by a greater distance and may have a greater temperature difference relative to each other, for instance 20° C. This is the result of the greater heat flow through the relatively thick block 2. Conversely, in a thinner embodiment of the block 2, several cooling stations 9 will have to be spaced more closely, with relatively small temperature differences, for instance 5° C. By giving the apparatus a modular construction, i.e. by incorporating each cooling station 9 or, possibly, a limited number of cooling stations 9 into a separate module, while the modules are equal and can be intercoupled thermally and mechanically, the advantage is achieved that such apparatus can be manufactured and built up in an economical manner. In terms of production, use and economy, a relatively thin block 2 may have advantages over a relatively thick block 2.

Of course, it is also possible to choose the rate of the containers 16 relative to the block 2 to be different, for instance 500 mm/min, together with a shorter block 2, for instance 800 mm. For this, a temperature gradient TG of 2° C./cm should then for instance be set. Thus, a relatively thin block 2 may suffice.

Figure 6:
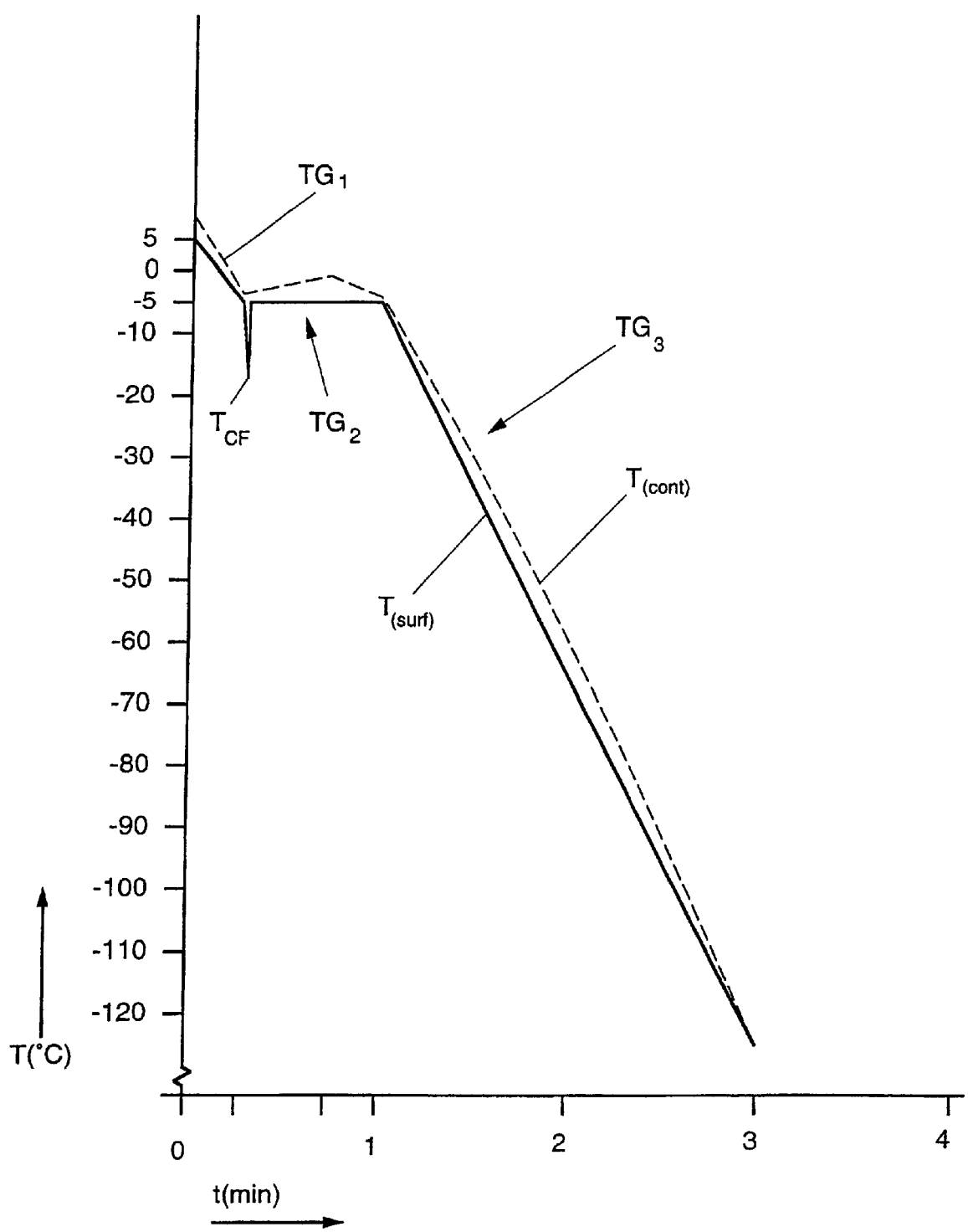
FIG. 6 is a schematic representation of a time-temperature protocol for an apparatus according to FIG. 5.

FIG. 5 shows an alternative embodiment of an apparatus 101 according to the invention. Identical parts have been designated by identical reference numerals. FIG. 6 shows an associated control diagram. When such apparatus is used, containers 116 can, during use, be disposed in stationary condition on a block 102 and cooled in order to freeze the samples included therein under ideal conditions.

The apparatus 101 comprises a block 102 manufactured from heat-conducting material such as metal, for instance aluminum, copper or alloys thereof, in which a number of cooling pipes 105 are included. The cooling pipes 105 are connected, via a number of control valves 107, to a feed pipe 106 for a cooling agent, for instance liquid nitrogen. Included in the surface 103 of the block 102 are thermostat means 108, connected to a central control unit 110. By means of the central control unit 110, the control valves 107 can be controlled for feeding through the cooling pipes 105 an amount of cooling medium adjusted to the temperature of the surface 103 desired at that moment, depending on the temperature measured. A cooling protocol CP, inputted in the central control unit 110 and adjusted to the live cells to be cooled, can thereby be transferred to the block 102 and, accordingly, to the containers 116 disposed thereon.

In this apparatus 101, too, the containers 116 disposed on the surface 103 are covered, during use, by means of a flexible, thermally insulating cover film 117, with the cooling pipes 105 opening between the surface 103 of the block 102 and the film 117. An apparatus according to FIG. 5 is in particular suitable for use with containers having a relatively small height compared with their surface, for instance film bags as are conventional for boar sperm (sperm of male pigs), but also for cells in trays or on slides. Provided in or above the surface 103 is a cooling finger 123, which can be briefly supercooled and contacted with a portion of the containers 116 disposed on the surface 103.

FIG. 6 schematically shows a control diagram for use with an apparatus 101 according to FIG. 5, in which identical parts have identical reference numerals. FIG. 6 graphically shows the relation between the temperature of the surface 103 and the temperature in the containers 116. A drawn line $T_{(surf)}$ shows the temperature profile obtained on the surface 103 during use, and a broken line $T_{(hold)}$ shows the temperature profile occurring in a container 16 disposed on the surface. Plotted out along the vertical axis is the temperature, in ° C., and plotted out along the horizontal axis is the time, in minutes. The values shown are merely intended as an illustration and have been selected for freezing boar sperm.

Before the start of the freezing path, the containers 116 are cooled down to, for instance, +5° C. Next, the containers 116 are placed on the surface 103 at time $t_1$, while or whereafter the surface temperature $T_1$ is set at −5° C. The containers 16 and each sample included therein are cooled ($TG_1$) until the temperature in the container is about −5°. Then, the cooling finger 123 is contacted with a portion of each container 116 and supercooled for initiating the crystallization in the containers. Next, the temperature of the surface 103 is maintained at −5° C. during a crystallization phase $T_2$ (temperature change gradient $TG_2=0$) until complete crystallization has taken place. After that, the temperature of the surface is gradually reduced to −120° C., for instance with an average temperature decrease $TG_3$ of 100° C./min to 150° C./min for bovine sperm or 50° C./min for boar sperm, to obtain a complete freezing of the samples. The samples can then be stored for later use, and the temperature of the surface 103 can again be returned to the starting temperature $T_1$ of −5° C.

An apparatus according to the invention comprises at least one contact face whose temperature is controllable by means of cooling and/or heating means. In this context, a contact face should be interpreted as a surface capable of influencing the temperature of containers through direct or at least almost direct contact. The temperature of the or each contact face itself may for instance be controlled through contact with a cooling medium, through convection or through radiation, while the or each container may abut against the contact face or may for instance be spaced therefrom by a very slight distance, for instance supported by a film of cooling medium.

The invention is by no means limited to the apparatuses and methods as described in the examples. Many variations thereto are possible.

For instance, depending on the type and amount of cells to be frozen, the desired accuracy, the desired chance of survival, the composition of the liquid or a different type of environment in which the live cells are accommodated and frozen, the desired final temperature and the like, a different freezing protocol may be selected. Moreover, other types of contact surfaces may be applied, for instance tubular guides in an apparatus according to FIGS. 1–3 or tubular or shell-shaped receiving recesses in an apparatus according to FIG. 5. Also, combinations of such surfaces may be used.

Further, an apparatus may be built up from a combination of an apparatus according to the invention for the first, generally most critical portion of the freezing path, and an apparatus of the known type for a portion of the freezing path after the crystallization phase, i.e. that part of the freezing path after which at least substantially complete crystallization has taken place in the containers. Further, other cooling means may be used and other containers may be employed. Also, several contact faces may be arranged so as to be opposite each other, with the containers being received or passed through between the relevant contact faces. The cooling protocol may be controlled manually or (semi-)automatically. These and many comparable variants fall within the framework of the invention.

What is claimed is:

1. An apparatus for freezing live cells which cells are included in at lease one sample in at least one container, the apparatus being provided with at least one cooler, the cooler comprising at least one contact face, capable of being cooled, for cooling, during use, the at least one container and the at least one sample included therein through at least abutting contact, wherein a controller is provided to control, during cooling, the cooling rate (TG) and the ambient temperature of the at least one container, wherein means are provided for moving the at least one container relative to the at least one contact face (3).

2. The apparatus of claim 1, wherein the controller is arranged for providing and maintaining, during use, a temperature difference over each contact face between the ends thereof that are located opposite one another in direction of movement, so that during use, the at least one container is moved in the direction of the coldest end.

3. The apparatus of claim 2, wherein the controller is arranged to set and keep set, during use in a crystallization sector of the apparatus, a relatively small temperature difference over the contact face or the contact face portion in the crystallization sector, the average temperature in the crystallization sector being such that crystallization occurs in the at least one container during its movement through the crystallization sector.

4. The apparatus of claim 1, wherein a series of contact faces are provided, each contact face having, during use, at least an average temperature ($T_1$–$T_9$) which is equal to or less than the contact face temperature which precedes it in the direction of movement.

5. The apparatus of claim 1 wherein the controller in or adjacent each contact face comprises a thermometer and a cooler, the cooler being controllable on the basis of a signal provided by the thermometer, for controlling the temperature over the relevant surface.

6. The apparatus of claim 4 wherein the apparatus comprises a number of modules, each module comprising at least one contact face and the modules being thermally coupled.

7. The apparatus of claim 1 wherein the contact face comprises a guide to direct the at least one container in a controlled manner along the at least one contact face.

8. The apparatus of claim 1, wherein the controller in or adjacent the contact face comprises at least a thermometer and a cooler, the cooler being controllable on the basis of a signal provided by the thermometer, for controlling the temperature of the relevant surface.

9. The apparatus of claim 1 wherein the cooler comprises cooling channels for passing through a cooling medium, and a valve means to control the amount of medium which, during use, flows through the cooling channels.

10. The apparatus of claim 9, wherein the apparatus comprises a substantially closed housing, the at least one container being cooled within the housing, at least a number of the cooling channels opening within the housing, the cooling medium being a gaseous cooling medium which, during or after leaving the cooling channels, changes into a gaseous phase, the arrangement being such that, during use, condensation is prevented by the gaseous cooling medium within the housing.

11. The apparatus of claim 10, wherein at least a number of the cooling channels open so that during use, the gaseous cooling medium moves through the housing, substantially in a direction opposite to the direction of movement of each container.

12. The apparatus of claim 1 wherein a cover is provided for covering, during cooling, each at least one container at the side remote from the contact face.

13. The apparatus of claim 2 wherein at the coldest side of the apparatus, means exist for sorting containers, discharging containers from the apparatus and storing containers.

14. The apparatus of claim 1 further including crystallization-initiation means.

15. A method for freezing live cells comprising the following steps:

including a sample comprising a number of live cells into a container;

placing the container in a cooling apparatus, in contact with a cooling surface;

controlled cooling of the containers through controlled cooling of the cooling surface, wherein;

in a first cooling path, the container is cooled relatively quickly until the start of crystallization occurs in the container;

in a second cooling path, relatively slow or no further cooling of the container takes place, until crystallization in the containers has occurred at least substantially completely; and in a third cooling path, the containers are cooled relatively quickly to at least a final temperature at which the cells are substantially chemically, biochemically and physically stable.

16. A method according to claim 15, wherein the container is moved along at least one contact face between a first end having a relatively high temperature, and a second end having a relatively low temperature, wherein the temperature gradient is accurately controlled along the at least one contact face according to a cooling protocol suitable for the particular live cells.

17. The apparatus of claim 2 wherein a series of contact faces are provided, each contact face having, during use, at least an average temperature ($T_1$–$T_9$) which is equal to or less than that of the contact face which precedes it in the direction of movement.

18. The apparatus of claim 3 wherein a series of contact faces are provided, each contact face having, during use, at least an average temperature ($T_1$–$T_9$) which is equal to or less than that of the contact face which precedes it in the direction of movement.

19. The apparatus of claim 2 wherein the controller in or adjacent each contact face comprises a thermometer and, associated therewith, a cooler, the cooler being controllable on the basis of a signal provided by the thermometer, for controlling the temperature.

20. The apparatus of claim 3 wherein the controller in, or adjacent, each contact face comprises a thermometer and associated cooler, the cooler being controllable on the basis of a signal provided by the thermometer, for controlling the temperature.

* * * * *